United States Patent [19]

Hagen et al.

[11] Patent Number: 4,544,755
[45] Date of Patent: Oct. 1, 1985

[54] CLEAVAGE OF PHTHALIMIDES TO AMINES

[75] Inventors: Helmut Hagen, Frankenthal; Rolf-Dieter Kohler, Edingen-Neckarhausen, both of Fed. Rep. of Germany

[73] Assignee: Basf Aktiengesellschaft, Ludwigshafen, Fed. Rep. of Germany

[21] Appl. No.: 613,227

[22] Filed: May 23, 1984

[51] Int. Cl.⁴ .................. C07D 233/58; C07C 85/20
[52] U.S. Cl. .......................... 548/335; 260/465 E; 544/165; 544/402; 548/164; 548/191; 548/199; 548/338; 549/61; 564/166; 564/329; 564/413
[58] Field of Search ............ 548/335, 338, 164, 199, 548/191; 260/465 E; 564/413, 329, 166; 544/165, 402; 549/61

[56] References Cited
PUBLICATIONS

Wolfe, S. et al., Can. J. Chem., 48, 3572–3579 (1970).

Primary Examiner—Richard A. Schwartz
Attorney, Agent, or Firm—Oblon, Fisher, Spivak, McClelland & Maier

[57] ABSTRACT

Phthalimides of the formula I

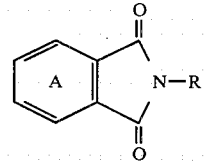

where R is a substituent and the ring A can be further substituted, are cleaved by a process in which a compound of the formula I is treated with an alkanolamine.

The compounds prepared according to the invention are useful intermediates for the preparation of dyes, drugs and plastics.

13 Claims, No Drawings

CLEAVAGE OF PHTHALIMIDES TO AMINES

The present invention relates to a process for the cleavage of phthalimides of the formula I

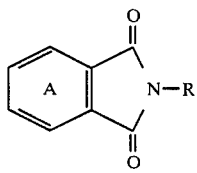

where R is a substituent and the ring A can be further substituted, wherein a compound of the formula I is treated with an alkanolamine.

R can be an aliphatic, cycloaliphatic, aromatic or heterocyclic group.

Examples of suitable radicals are alkyl which is unsubstituted or substituted by alkoxy, cyano, carboxamido, unsubstituted or substituted amino or aryl; cycloalkyl; aryl which is unsubstituted or substituted by halogen, nitro, alkyl, alkoxy, cyano, carbamyl, formyl, sulfamyl, cyanomethyl, alkoxymethyl, aryloxymethyl, arylthiomethyl, arylsulfonylmethyl, aryl, benzoyl, vinylaryl, vinylimidazolyl or carboxyl; saturated or unsaturated heterocyclic radicals; and alkenyl.

Examples of specific radicals R are: $CH_3$, $C_2H_5$, $C_3H_7$, $C_4H_9$, $C_5H_{11}$, $C_6H_{13}$, $C_7H_{15}$, $C_8H_{17}$, $C_{10}H_{21}$, $C_{12}H_{25}$, $C_2H_4OCH_3$, $C_2H_4OC_4H_9$, $C_4H_8OCH_3$, $(CH_2)_5CN$, $C_2H_4N(CH_3)_2$, $C_6H_4Cl$, $C_6H_4NO_2$, $C_6H_4CH_3$, $C_6H_4OCH_3$, $C_6H_3Cl_2$, $C_6H_3(NO_2)_2$, $C_6H_4CN$, $C_6H_4COOH$, $C_6H_4CONH_2$, $C_6H_4CHO$, $C_6H_4SO_2C_6H_5$, $C_6H_4CH_2CN$, $C_6H_4OCH_3$, $C_6H_4CH_2OCH_3$, $C_6H_4CH_2SCH_3$, $C_6H_4CH_2SC_6H_5$, $C_6H_4CH_2SO_2C_6H_5$, $C_6H_5$, $C_6H_4COC_6H_5$ and $C_2H_4C_6H_5$.

The ring A can be further substituted by, for example, chlorine, bromine, nitro, carboxyl, carbamyl or sulfamyl.

The compounds of the formula I can be prepared by a conventional method, for example by reacting a halogen compound with potassium phthalimide by the Gabriel method.

The cleavage of the phthalimides to give amines and phthalic acids or derivatives thereof is frequently very difficult in practice. Acidic hydrolysis with 20–30% strength hydrochloric acid generally requires prolonged refluxing (Liebig Ann. Chem. 1949, 22) or has to be carried out at 200° C. under superatmospheric pressure (Chem. Ber. 20 (1887), 2224). Alkaline hydrolysis with an aqueous alkali does not in general proceed any further than the phthalamic acid stage. For complete hydrolysis, a downstream treatment with a mineral acid is necessary (Chem. Ber. 37 (1904), 1038). Although the cleavage of the phthalimides of the formula I by means of hydrazine presents scarcely any problems on the laboratory scale, considerable difficulties are encountered on an industrial scale. The sparingly soluble salt of the cyclic phthalic hydrazide is formed in the reaction (Nature (London) 158 (1946), 514) and separates out as a bulky precipitate, the handling of which requires large amounts of solvents and large reaction kettles. The acute toxicity and the high price of hydrazine are also obstacles to the economical use of this method.

It was therefore extremely surprising that cleavage of phthalimides can be carried out readily in accordance with the invention.

The cleavage of the phthalimide of the formula I is carried out simply by heating the compound in an alkanolamine. This acts both as a solvent and as a reactant. Examples of suitable alkanolamines are monoethanolamine, monoisopropanolamine, 3-aminopropanol and aminoethylethanolamine. Monoethanolamine is preferably used. The reaction temperatures are from 40° to 140° C., preferably from 60° to 100° C. The method of working up the reaction mixture depends on the nature of the amine liberated, and is as a rule very simple. For example, water-insoluble, solid amines can usually be precipitated by adding water. Water-soluble amines can be isolated by extraction with a solvent, such as methylene chloride, ethyl acetate or toluene. The phthalic acid alkanolamides liberated in the reactions remain in the aqueous phase and can therefore be separated off without difficulty.

The cleavage can of course also be carried out in the presence of an additional solvent, this being done in particular where the cleavage products are capable of reacting with the alkanolamines, so that an excess of alkanolamine over and above the stoichiometric amount is disadvantageous. For example, where exchangeable halogen atoms are present, it is advisable to carry out the reaction only with about the stoichiometric amount of the alkanolamine.

Examples of solvents which can be used in the cleavage are alkanols, glycols, glycol ethers, ketones, halohydrocarbons or hydrocarbons, specific examples being methanol, ethanol, propanol, butanol, glycol, methyl glycol, ethyl glycol, acetone, methyl ethyl ketone, tetrahydrofuran, dioxane, methylene chloride, chlorobenzene and toluene.

As a rule, the phthalimido radical serves as a protective group, i.e. its presence permits reactions which are impossible in the presence of a free amino group. For example, when the amino group is protected it is possible to carry out alkylations, acylations, nitrations, halogenations, chlorosulfonations or oxidations.

The novel process is particularly useful in the case of compounds possessing aromatic or heteroaromatic radicals R, in particular phenyl, naphthyl, thiazolyl, thiadiazolyl, imidazolyl, benzothiazolyl, benzimidazolyl, indolyl, pyridyl or quinolyl radicals.

EXAMPLE 1

2-Aminobenzylcyanide 100 g of 2-cyanomethyl-N-phenylphthalimide were introduced, a little at a time, into 100 g of monoethanolamine at 80° C. After 10 minutes, the mixture was cooled to 20° C., and 400 g of ice water were added dropwise. The precipitated product was filtered off under suction and washed neutral with ice water.

Yield: 40 g (80% of theory); m.p. 70° C.

EXAMPLE 2

1-(2-Aminobenzyl)-imidazole 30 g of 2-(1-imidazolylmethyl)-N-phenylphthalimide in 60 g of monoethanolamine were stirred for 1 hour at 70° C. The mixture was cooled to 20° C., after which 200 g of ice water were added dropwise and the mixture was extracted with three times 150 g of ethyl acetate. The combined extracts were dried, and evaporated down under reduced pressure.

Yield: 13 g (75% of theory); m.p. 42° C.

EXAMPLE 3

4,4'-Diaminobenzophenone 20 g of bis-[4,4'-(carboxyphthalimidoyl)]-benzophenone in 30 g of monoethanolamine were stirred for 15 minutes at 80° C., after which 200 g of ice water were added dropwise at 20° C. The precipitate was filtered off under suction, washed with water and dried.

Yield: 7 g (92% of theory); m.p. 236° C.

The following amines were prepared from the compounds of the formula I, using methods similar to those described in Examples 1 to 3:

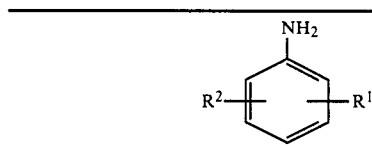

| Example | $R^1$ | $R^2$ | mp. [°C.] |
|---|---|---|---|
| 4 | 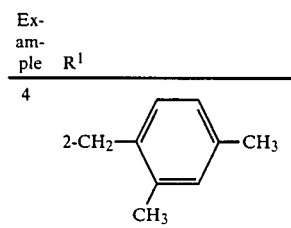 2-CH$_2$-, with CH$_3$ and CH$_3$ substituents | H | 38 |
| 5 | 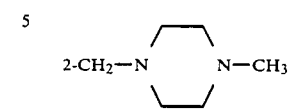 2-CH$_2$-N(ring)N-CH$_3$ | H | 86 |
| 6 | 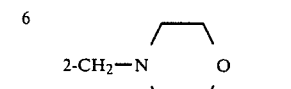 2-CH$_2$-N(ring)O | H | 64 |
| 7 | 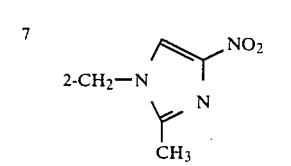 2-CH$_2$-N with NO$_2$, N, CH$_3$ | H | 150 |
| 8 | 2-CN | H | 48 |
| 9 | 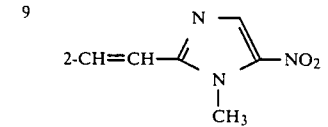 2-CH=CH-(ring with N, N-CH$_3$, NO$_2$) | H | 223 |
| 10 | 2-CH$_2$OCH$_3$ | H | oil |
| 11 | 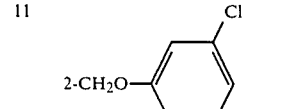 2-CH$_2$O-(C$_6$H$_4$-Cl) | H | 90 |
| 12 | 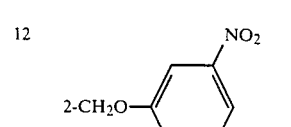 2-CH$_2$O-(C$_6$H$_4$-NO$_2$) | H | 106 |
| 13 | 2-CH$_2$SH | H | oil |

-continued

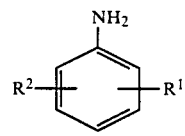

| Example | $R^1$ | $R^2$ | mp. [°C.] |
|---|---|---|---|
| 14 | 2-CH$_2$S—C$_6$H$_5$ | H | 75 |
| 15 | 2-CH$_2$SO$_2$—C$_6$H$_5$ | H | 178 |
| 16 | 2-CH$_2$N(ring)O | 3-Cl | 76 |
| 17 | 2-CH$_2$OCH$_3$ | 3-Cl | oil |
| 18 | 2-CH$_2$O-(C$_6$H$_4$-NO$_2$) | 3-Cl | 97 |
| 19 | 2-CH$_2$O-(C$_6$H$_4$-NO$_2$) | 3-Cl | 158 |
| 20 | 2-CH$_2$SO$_2$C$_6$H$_5$ | 6-CH$_2$SO$_2$C$_6$H$_5$ | 216 |
| 21 | 2-CH$_2$C(=O)NH$_2$ | 4-NO$_2$ | 227 |
| 22 | 2-CH$_2$N(C$_2$H$_5$)(C$_6$H$_5$) | H | 72 |
| 23 | 2-CH$_2$N(ring)N-CH$_2$-(C$_6$H$_4$-NH$_2$) | H | 201 |
| 24 | 2-CH=CH—CN | 4-NO$_2$ | 266 |
| 25 | 2-CHO | 4-NO$_2$ | 200 |
| 26 | 2-CHO | 4-Cl | 90 |
| 27 | 2-CH$_2$OH | 3-Cl | 75 |
| 28 | 2-CN | 4-NO$_2$ | 209 |

The following heterocyclic amines can also be prepared by methods similar to those described:

2-amino-4-phenylthiazole,
2-amino-5-nitrothiazole,
2-amino-3-cyano-4-methyl-5-aminocarbonylthiophene and
2-amino-5-nitrobenzothiazole.

We claim:

1. A process for the cleavage of a phthalimide of the formula I

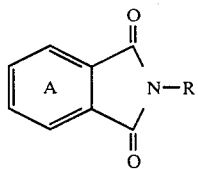

to produce H₂N—R;

wherein R is an aliphatic, cycloaliphatic, aromatic or heterocyclic group, and ring A is either unsubstituted or independently substituted by chlorine, bromine, nitro, carboxyl, carbamyl or sulfamyl;

wherein the compound of formula I is treated with an alkanol amine.

2. The process of claim 1, wherein R is an alkyl radical which is either unsubstituted or substituted by an alkoxy, a cyano, a carboxamido, or an unsubstituted or substituted amino or aryl group.

3. The process of claim 1, wherein R is a cycloalkyl radical.

4. The process of claim 1, wherein R is an aryl substituent which is either unsubstituted or substituted by a halogen, a nitro, an alkyl, an alkoxy, a cyano, a carbamyl, a formyl, a sulfamyl, a cyanomethyl, an alkoxymethyl, an aryloxymethyl, an arylthiomethyl, an arylsulfonylmethyl, an aryl, a benzoyl, a vinylaryl, a vinylimidazolyl or a carboxyl group.

5. The process of claim 1, wherein R comprises a saturated or an unsaturated heterocyclic radical.

6. The process of claim 1, wherein R is an alkenyl.

7. The process of claim 1, wherein R comprises $CH_3$, $C_2H_5$, $C_3H_7$, $C_4H_9$, $C_5H_{11}$, $C_6H_{13}$, $C_7H_{15}$, $C_8H_{17}$, $C_{10}H_{21}$, $C_{12}H_{25}$, $C_2H_4OCH_3$, $C_2H_4OC_4H_9$, $C_4H_8OCH_3$, $(CH_2)_5CN$, $C_2H_4N(CH_3)_2$, $C_6H_4Cl$, $C_6H_4NO_2$, $C_6H_4CH_3$, $C_6H_4OCH_3$, $C_6H_3Cl_2$, $C_6H_3(NO_2)_2$, $C_6H_4CN$, $C_6H_4COOH$, $C_6H_4CONH_2$, $C_6H_4CHO$, $C_6H_4SO_2C_6H_5$, $C_6H_4CH_2CN$, $C_6H_4OCH_3$, $C_6H_4CH_2OCH_3$, $C_6H_4CH_2SCH_3$, $C_6H_4CH_2SC_6H_5$, $C_6H_4CH_2SO_2C_6H_5$, $C_6H_5$, $C_6H_4COC_6H_5$ or $C_2H_4C_6H_5$.

8. The process of claim 1, wherein the alkanolamine is at least one member selected from the group consisting of mono-ethanolamine, mono-isopropanolamine, 3-aminopropanol and aminoethylethanol amine.

9. The process of claim 1, wherein the alkanolamine is mono-ethanolamine.

10. The process of claim 1, wherein the reaction is run at a temperature of from 40° to 140° C.

11. The process of claim 10, wherein the reaction is run at a temperature of from 60° to 100° C.

12. The process of claim 1, wherein said process is run in a solvent which comprises an alkanol, a glycol, a glycolether, a ketone, a halohydrocarbon or a hydrocarbon.

13. The process of claim 12, wherein the solvent is at least one member selected from the group consisting of methanol, ethanol, propanol, butanol, glycol, methylglycol, ethylglycol, acetone, methylethylketone, tetrahydrofuran, dioxane, methylenechloride, chlorobenzene and toluene.

* * * * *